US006392097B1

(12) United States Patent
Dolbier, Jr. et al.

(10) Patent No.: US 6,392,097 B1
(45) Date of Patent: May 21, 2002

(54) PROCESS FOR THE PREPARATION OF DERIVATIVES OF OCTAFLUORO-[2,2] PARACYLOPHANE

(75) Inventors: William R. Dolbier, Jr.; Jian-Xin Duan, both of Gainesville, FL (US); Alex J. Roche, Haddonfield, NJ (US)

(73) Assignee: Specialty Coating Systems, Inc., Indianapolis, IN (US)

( * ) Notice: Subject to any disclaimer, the term of this patent is extended or adjusted under 35 U.S.C. 154(b) by 0 days.

(21) Appl. No.: 09/812,514

(22) Filed: Mar. 20, 2001

Related U.S. Application Data
(60) Provisional application No. 60/190,778, filed on Mar. 20, 2000.

(51) Int. Cl.$^7$ ............................................. C07C 209/00

(52) U.S. Cl. ........................ 564/411; 564/306; 564/308; 570/124; 570/127; 570/129; 570/143; 570/144

(58) Field of Search ................................ 570/124, 127, 570/129, 143, 144; 564/306, 308, 411

(56) References Cited

U.S. PATENT DOCUMENTS

| 5,210,341 A | * | 5/1993 | Dolbier et al. | ............... 570/144 |
| 5,849,962 A | * | 12/1998 | Dolbier et al. | ............... 570/144 |
| 6,194,620 B1 | * | 2/2001 | Maruyama | .................. 570/127 |

* cited by examiner

*Primary Examiner*—Alan Siegel
(74) *Attorney, Agent, or Firm*—Barry J. Marenberg, Esq.; Mintz, Levin, Cohn, Ferris, Glovsky and Popeo

(57) ABSTRACT

Processes for the preparation of parylene dimers, and more particularly to processes for the preparation of derivatives of octafluoro-[2,2]paracylophane, otherwise known as AF4.

16 Claims, No Drawings

PROCESS FOR THE PREPARATION OF DERIVATIVES OF OCTAFLUORO-[2,2] PARACYLOPHANE

This application claims benefit of application Ser. No. 60/190,778 filed Mar. 20, 2000.

FIELD OF THE INVENTION

The present invention relates generally to processes for the preparation of parylene dimers, and more particularly to processes for the preparation of derivatives of octafluoro-[2,2]paracylophane, otherwise known as AF4.

BACKGROUND AND SUMMARY OF THE INVENTION

Parylene is a generic term used to describe a class of poly-p-xylylenes which are derived from a dimer having the structure:

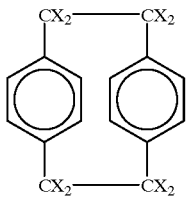

wherein X is typically a hydrogen, or a halogen. The most commonly used forms of parylene dimers include the following:

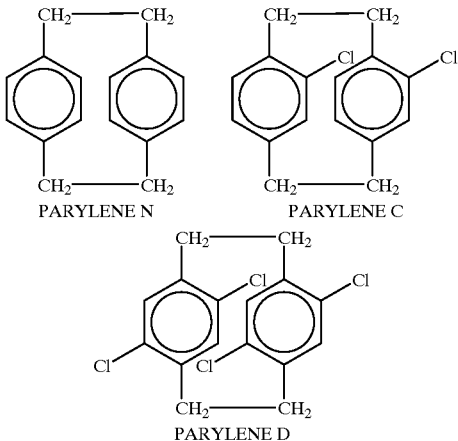

Parylene coatings are obtained from parylene dimers by means of a well-known vapor deposition process in which the dimer is vaporized, pyrolized, i.e. cleaved into a monomer vapor for, and fed to a vacuum chamber wherein the monomer molecules polymerize, and deposit onto a substrate disposed within the vacuum chamber.

Due to their ability to provide thin films and conform to substrates of varied geometric shapes, parylene materials are ideally suited for use as a conformal coating in a wide variety of fields, such as for example, in the electronics, automotive, and medical industries.

Parylene polymers are usually formed by chemical vapor deposition (CVD) processes. One such process is the Gorham process in which a parylene dimer having the molecular structure:

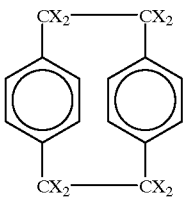

is vaporized and the dimer bonds are then cleaved to yield parylene monomers. The parylene monomers are deposited onto a surface and subsequently polymerized. Because the dielectric constant and melting temperature of parylene polymers usually increases as the number of fluorine atoms within the polymer increases, it is desirable to use octafluoro-[2,2]paracylcophane (AF4).

Octafluoro-[2,2]paracyclophane, more precisely 1,1,2,2, 9,9,10,10-Octafluoro-[2,2]paracyclophane, and more commonly referred to in the industry as AF4, is a fluorine substituted version of the above-noted dimers and has the structure:

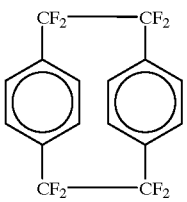

It is known that parylene coatings (Parylene $AF_4$) which are derived from the $AF_4$ dimer by the vapor deposition process have a very high melting temperature (about 540° C.), and a low dielectric constant (about 2.3). These characteristics make Parylene $AF_4$ ideally suited for many high temperature applications, including electronic applications, and potentially as an inter-layer dielectric material for the production of semiconductor chips. However, up to the present time, AF4, which is used as the dimer starting material for depositing Parylene F coatings, has been commercially unavailable due to high costs of production. Both OFP and AF4 are used interchangeably herein and are intended to refer to the same compound.

One known method of producing AF4 is described in U.S. Pat. No. 5,210,341 wherein the process of preparing AF4 utilizes a low temperature in conjunction with a reduced form of titanium in order to produce dimerization of dihalide monomers. One aspect of the '341 patent provides a process for preparing octafluoro-[2,2]paracyclophane, which comprises contacting a dihalo-tetrafluoro-p-xylylene with an effective amount of a reducing agent comprising a reduced form of titanium and an organic solvent at conditions effective to promote the formation of a reaction product comprising octafluoro-[2,2]paracyclophane.

While the process described in the '341 patent is effective for its intended purpose, it has been found that the process is still too expensive for commercial realization due to low yields, that there are some impurities in the AF4 dimer, and furthermore that it would be difficult to adapt to a large scale commercial production.

TFPX-dichloride having the following structure:

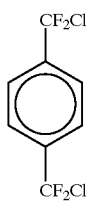

is another preferred starting material for the preparation of AF4. Heretofore, the only useful preparation of TFPX-dichloride has been via a high yield, photo-induced chlorination of α,α,α',α'-tetrafluoro-p-xylene (hereinafter "TFPX") having the molecular structure:

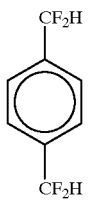

The conventional procedure for synthesizing TFPX involves the fluorination of terephthaldehyde, which has the molecular structure:

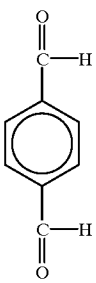

$SF_4$ and $MoF_6$ are the most commonly used reagents for terephFthaldehyde fluorination. However, $SF_4$ and $MoF_6$ are expensive, reducing the industrial utility of this synthetic scheme. In addition, $SF_4$ and $MoF_6$ are toxic materials, so a large amount of hazardous waste is produced using these reagents.

Russian patent 2,032,654 discloses an alternative method of synthesizing TFPX in which α,α,α',α'-tetrabromo-p-xylene (hereinafter "TBPX") having the molecular structure:

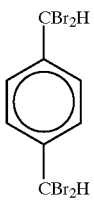

is reacted with $SbF_3$ to produce TFPX. This method employs the well established electrophilic catalyzed $S_N1$ reaction mechanism for replacement of benzylic halogen atoms of the TFPX with fluorine atoms. According to this method, the anitmony in $SbF_3$ acts as an elctrophile which removes bromine from TBPX to form a carbocation. The carbocation subsequently reacts with fluorine to form TFPX. While this reaction is reported to provide good yield when carried out under comparatively mild reaction conditions, antimony containing compounds are highly toxic and explosive. Furthermore, the $SbF_3$ is used in a stoichiometric amount rather than a catalytic amount, resulting in large quantities of hazardous waste materials. This method of synthesizing TFPX thus has limited use for industrial applications.

AF4 is a member of the class of paracyclopenones. Paracyclophenone (PCP) chemistry has grown considerably since the isolation of the parent compound in 1949. Braun et al., NATURE (1949) 164, 915. Besides finding commercial application as monomers for the parylene type polymers, these molecules have spawned an unusual and unique chemistry. The close proximity of the face-to-face aromatic rings, coupled with the rigid skeleton and high strain energy translates into such effects as trans-annular interactions, thermal racemization and isomerism, surprising directing effects in multiple electrophilic substitution and unusual spectroscopic phenomena. The use of ring-substituted [2,2] PCP skeletons as chiral backbones is of considerable current interest. Highly fluorinated cyclophanes on the other hand, have received much less attention, even though these compounds have desirable industrial properties and should at least display as equally rich a chemistry as their hydrocarbon counterparts. This imbalance is being redressed following the syntheses of the bridge fluorinated cyle 1,1,2,2,9,9,10,10 octafluoro[2,2]paracyclophane (abbreviated as OFP, and more commonly referred to in the industry as AF4) that have been reported previously.

Two complementary synthetic methods for the introduction of two substituents into the rings of octaflouroparayclophane have thus been developed. Nitration gives three isomers with the nitro functionalities in different rings, oriented pseudo meta, pseudo para and pseudo ortho. Bromination on the other hand gives a dibromide where both halogens are in the same ring, para to each other. All such products serve as versatile starting materials for the preparation of a variety of novel homo- and hetero-annular disubstitututed OFP derivatives. The compounds synthesized have also been found to be precursors of a variety of other disubstituted OFP derivatives. The synthesis, characterization and thermal isomerization of a variety of both homo- and hetero-annularly disubstituted OFP derivatives has also been developed and described.

The instant invention provides improved processes for the preparation of octafluoro-[2,2]paracyclophane which involve contacting a OFP with dry nitrogen, nitronium tetrafluoroborate dissolved in sulphophane to provide pseudo meta-, pseudo para-, and pseudo ortho-dinitro-1,1, 2,2,9,9,10,10-octafluoroparacyclophanes. Reduction of these three products using iron powder/concentrated hydrochloric acid provided the corresponding diamino products in good isolated yields. The three diamino products proved to be versatile starting materials for further transformations by reacting with an aqueous solution of copper (I) bromide and hydrobromic acid or an aqueous solution of potassium iodide to provide three isomeric dibromo and diiodo-OFP derivatives in good yield.

Accordingly, among the objects of the instant invention are: the provision of improved processes for the preparation of octafluoro-[2,2]paracyclophane; and more specifically, the provision of improved processes for the preparation of octafluoro-[2,2]paracyclophane from novel OFP precursor derivatives.

Other objects, features and advantages of the invention shall become apparent as the detailed description thereof proceeds.

DETAILED DESCRIPTION OF THE INVENTION

The present invention relates to highly thermally stable derivatives and precursors of octafluoro[2,2] paracyclophenone (AF4) and their preparation.

The nitration of AF4 gives a mononitro product in high yield. However, when such nitration is carried out under the more forcing conditions of five equivalents of $NO_2BF_4$ and a temperature of 80° C. (step i), the products generated are observed to be a mixture of three isomeric dinitro derivatives in over 80% combined isolated yield, with the ratio of the isomers being 1:1:1.

One of the isomers could be separated from the other two by column chromatography since it displayed a lower $R_f$ value than the other two, which co-eluted. The quicker running mixture of the two isomers could be enriched in one or the other isomer by fractional crystallization or sublimation. The $^{19}F$ NMR spectrum of each isomer showed only 2 AB patterns. The $^{19}F$ NMR spectra of AF4 consists of a singlet, and that mononitro-AF4 appears as 4 AB patterns. The increase in the symmetry of these new products relative to mono-nitro-AF4 indicated incorporation of at least two nitro groups.

Mass spectrometry confirmed not only that the products did indeed contain two nitro groups, but also that they were located on different rings. The relative orientation of the nitro groups in each of the three isomers was established through $^1H$ NMR, and further confirmed by thermal isomerizations and correlation of their physical properties with those already established for hetero-annularly disubstituted [2,2] PCP derivatives. The products were identified as pseudo-meta-, pseudo-para- and pseudo-ortho-dinitrooctafluoroparacyclophanes 2a–c, as illustrated in Scheme 1. No evidence of the pseudo-geminal isomer was observed, although as little as 1% could have been detected.

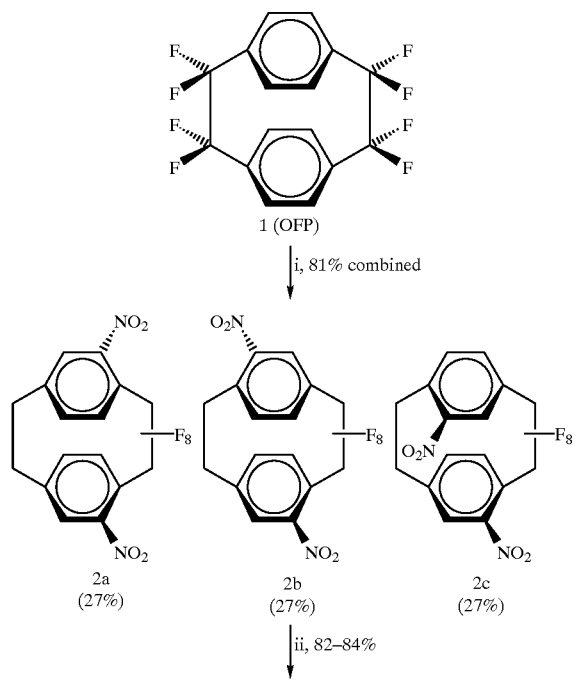

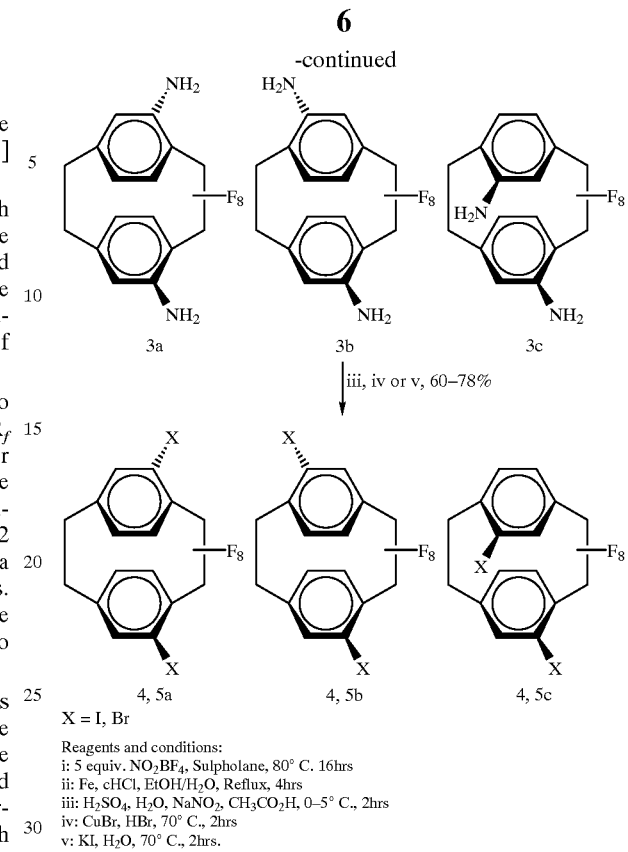

X = I, Br

Reagents and conditions:
i: 5 equiv. $NO_2BF_4$, Sulpholane, 80° C. 16hrs
ii: Fe, cHCl, EtOH/$H_2O$, Reflux, 4hrs
iii: $H_2SO_4$, $H_2O$, $NaNO_2$, $CH_3CO_2H$, 0–5° C., 2hrs
iv: CuBr, HBr, 70° C., 2hrs
v: KI, $H_2O$, 70° C., 2hrs.

The introduction of a nitro functionality into one ring deactivates that ring to further electrophilic substitution and guides subsequent reaction to the other unsubstituted ring. The lack of a pseudo geminal isomer is somewhat surprising since there are many examples of complete (or predominant) pseudo geminal electrophilic aromatic substitutions promoted by the substituents bearing basic functionalities, through their participation as intramolecular bases. Nitrations, however, are known to be less susceptible to such kinetic effects, in comparison to brominations, for example. The inventors have proposed that the lack of such a dinitro isomer in this reaction is due to steric effect. The nitration of the hydrocarbon [2,2] PCP using nitric acid at 75° C. is reported to yield mononitro [2,2] PCP (26%), and pseudo-meta (2%), pseudo-para (2%), pseudo-ortho (1.4%) and pseudo-geminal (0.7%) dinitro isomers.

The inventors have previously demonstrated that nitro-AF4 provides a route to a variety of ring substituted AF4 derivatives and similar synthetic methodologies can be applied here that allow the generation of a number or inter-annularly disubstituted AF4. See Roche et al., J. ORG. CHEM. 1999, 64, 9137.

The reactions in Scheme 1 were all performed on both single isomers and mixtures of the three isomers. The pseudo ortho isomer could always be separated from the pseudo meta/pseudo para mixture by column chromatography, regardless of the substituents. The pseudo meta/pseudo para isomers were, in general, unable to be separated by column chromatography. All reaction yields were essentially the same whether preformed on single or multiple isomers, and are comparable to the corresponding reactions used to make the monosubstituted AF4 analogues. The only difference in reactivity for the three disubstituted isomers in the reactions in Scheme 1 was observed in their trifluoromethylation reactions, where pseudo ortho duiodo isomer gave lower conversions and slower reactions. No isomerism or loss of integrity of the AF4 skeleton was observed during any of these reactions, although deliberate high temperature isomerization of selected examples of these compounds was studied.

The reduction of 2a–c using iron powder/conc. hydrochloric acid (step ii) gave the corresponding diamino products 3a–c in good isolated yields (82–84%). Cyclophanes containing electron donating substituents in one ring and electron acceptors in the other ring are often reported to be colored, and the corresponding inter-annular nitro-amino systems for the hydrocarbon [2,2] PCP vary from yellow to red, depending on the relative orientation of the two substituents. In an attempt to generate 6 (Scheme 2) with an amino group in one ring and a nitro group in the other, the milder reducing agent of cyclohexene and Pd on carbon was used in conjunction with 2c. Besides the corresponding diamino AF4 3c (38%), the nitroamino derivative 6 (11%) was isolated, and the hydroxyl-amino product 7 (15%).

Scheme 2

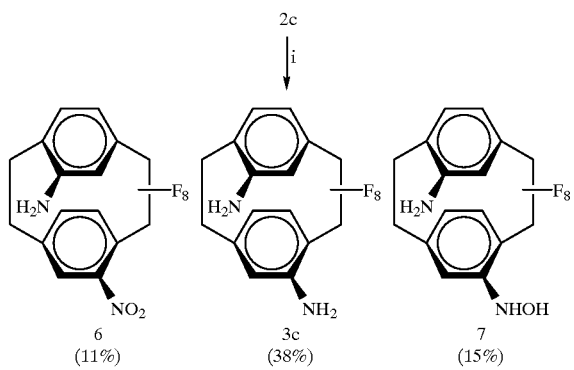

Reagents and conditions, i: Cyclohexane, Pd/C, EtOH, Reflux, 15mins

Dissapointingly, 6 was a white solid, in contrast to the orange/yellow color of the corresponding [2,2] PCP compound. This difference can be attributed to the electron density from the interacting 7 systems by the electron withdrawing fluoroalkyl bridging units, thus reducing charge transfer.

The diamino AF4 isomers 3a–c proved to be versatile starting materials for further transformations, with the most straightforward being the formation of the respective N-acetyl and -triflouroacetyl-amides in high isolated yield (84–97%). These compounds proved not only useful for characterization purposes, but also as protecting groups which moderated the reactivity of the diamino AF4 systems, and thus made appropriate materials for the high temperature thermal isomserization studies described infra herein.

The double diazotization of these diamino-systems proved as successful diazotization of monoamino-AF4, and thus the three isomeric dibromo (5a–c) and diiodo-AF4 (4a–c) derivatives were prepared in good isolated yield (60–78%) via Sandmeyer type chemistry (steps iii, iv, v in Scheme 1). The hetero-annular dibromides proved useful for comparison purposes when a homo-annular dibromide was later prepared. The hetero-annular dibromides also served as useful intermediates for further transformations, although the diiodes generally gave higher yields in such reactions, and were therefore the more desirable starting materials.

Triflouromethylation of the pseudo meta and pseudo para AF4 diiodides 4a,b gave moderate yields of corresponding bis(triflouromethylated) products 8a,b (50%) (Scheme 3), along with appreciable amounts of monotrifluoromethylated product 10 (30%) (Scheme 4). It was also observed that the addition of palladium dichloride provided vast improvements in the yields of bis(triflouromethylated) products (80%), and a consequent decrease in chemically reduced side products (Scheme 4).

Scheme 3

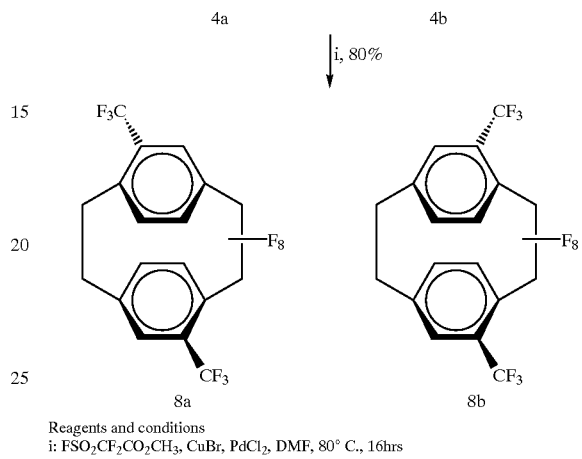

Reagents and conditions
i: FSO$_2$CF$_2$CO$_2$CH$_3$, CuBr, PdCl$_2$, DMF, 80° C., 16hrs When a typical uncatalyzed triflouromethylation was performed on pseudo ortho AF4 diiodide 4c (Scheme 4), the only two products obtained besides starting materials were identified as 10 (33%) and pseudo ortho iodo-triflouromethyl OFP 9 (21%). However, the addition of PdCl$_2$ promoted a superior reaction with the pseudo ortho bis(trifluoromethyl) derivative, 8c, being isolated in 68% yield, along with a 10% yield of iodo-triflouromethyl derivative, 9, which could itself be reduced by zinc in acetic acid to form triflouromethyl-AF4 (91%).

Scheme 4

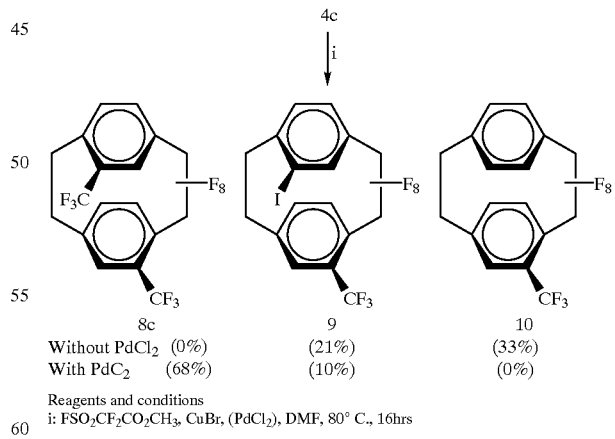

Without PdCl$_2$ (0%) (21%) (33%)
With PdCl$_2$ (68%) (10%) (0%)

Reagents and conditions
i: FSO$_2$CF$_2$CO$_2$CH$_3$, CuBr, (PdCl$_2$), DMF, 80° C., 16hrs The difference in reactivity displayed by the isomeric diiodides can be best understood in terms of the iodides simply being located either on the same or different sides of the cyclophane. Although exchange of triflouromethyl for iodine should make the iodo-triflouromethyl intermediate compounds more reactive toward further substitution, clearly this is not the case for the pseudo ortho isomer. It is likely that the two reaction centers in the pseudo ortho isomers are so close that when one iodine is replaced by a trifluoromethyl group, there is sufficient steric and electronic shielding by the attached trifluoromethyl group to inhibit further substitution. Having observed through space NMR interaction between syn bridging flourines and a triflouromethyl substituent on the ring, the inventors believe that these syn bridge fluorines also provide steric and electrostatic shielding to an attacking nucleophile. The use of a relatively large transition metal catalyst like Pd(III) may serve to reduce such steric constraints on the incoming nucleophile by coordinating the substrate and the nucleophile before joining them through a reductive elimination, thus resulting in the superior observed yields of triflouromethylyated products in PdCl$_2$ catalyzed reactions.

The pseudo ortho diiodide 4c was also used to produce the corresponding diphenyl derivative via reaction with phenyl magnesium bromide and PdCl$_2$, providing the diphenyl derivative in 21% yield along with 20% monophenyl-AF4. Identical mono and diphenylated products were also obtained via diazonium chemistry and benzene.

Although the overall yields of the diiodides and dibromides were acceptable for a three step procedure (40–53% isolated from AF4) as in Scheme 1, a direct bromination procedure to dibrominate OFP would be much more desirable. To this end, AF4 was subjected to several known bromination methods. However, the only method that was successful in generating more than a trace of dibromo-AF4 was a method recently reported by the inventors for bromination of deactivated aromatics. See Duan et al., SYNLETT (1999), 1245.

When triflouroacetic acid solution of AF4 was exposed to a combination of four equivalents of NBS and sulfuric acid at 80° C., a single major product was produced. The presence of 2AB patterns in the $^{19}$F NMR of this compound led to the belief that the product was a dibromide. The isolated yield of this compound, after column chromatography, was 55%m and somewhat surprisingly, the NMR of the product did not match any of those of the three inter-annular dibromides that had been prepared via the nitration/reduction/diazonium chemistry described hereinabove. Mass spectrometry revealed that the product was indeed a dibromide isomer, but that the bromines were both on the same ring. This information, coupled with the $^1$H and $^{19}$F NMR patterns (described infra.) indicated that this was para dibromo AF4, 5d.

A bromine susbtituent is normally viewed as a deactivating and ortho/para directing substituent in electrophilic aromatic substitution, and usually a deactivating substituent would guide subsequent substitution into the other ring of a [2,2] PCP. This was not, however, the case for this reaction, although the second bromine did enter para to the first.

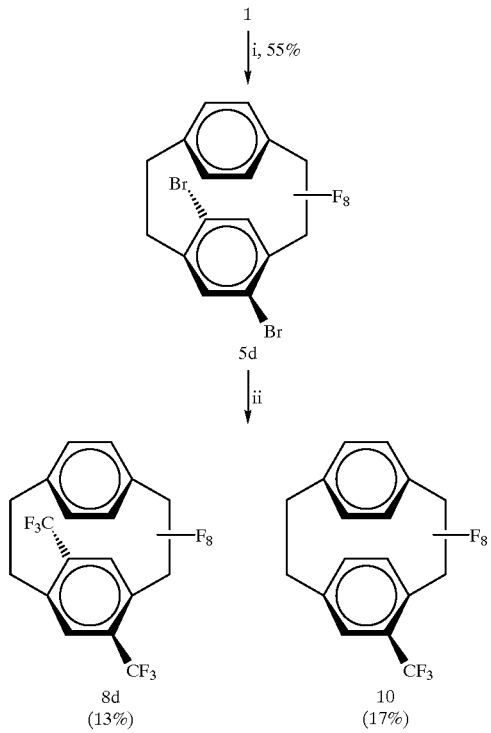

Scheme 5

8d (13%)   10 (17%)

Reagents and conditions
i: NBS, CF$_3$CO$_2$H, H$_2$SO$_4$, 80° C., 16hrs
ii: FSO$_2$CF$_2$CO$_2$CH$_3$, CuBr, DMF, 100° C., 14hrs.

With p-dibromo AF4 (5d) in hand, it was then possible to prepare the p-bis(triflouoromethyl) AF4 derivative, 8d, (Scheme 5) albeit in lower yields than had been obtained for the hetero-annular diiodides, 4c. As expected, the NMR spectra of 8d were also distinctively different from those of 8a, 8b, and 8c.

Thermal Isomerizations

The [2,2] PCP skeleton is rigid, and under normal conditions, maintains its integrity allowing, for example, the application of [2,2] PCP derivatives as chiral ligands and molecular scaffolds of known fixed geometry.[5] This holds true for temperatures below 150–200° C. Above these temperatures, ring substituted [2,2] PCP derivatives exhibit a thermal isomerization which is unique to this system. Typically, the deliberate isomerizations have been performed without solvent at 200° C. for 24 hours. It has been demonstrated that they proceeded though a bibenzyl type diradical intermediate. Reich et al., AM. CHEM. SOC. (1969) 91, 3517.

One might expect the longer C—C bridge length in OFP (1.577 Å) relative to [2,2] PCP (1.569 Å) to allow the racemization of AF4 derivatives to occur at lower temperatures since it is this bond that must break and reform. Conversely, since replacement of hydrogen by fluorine in saturated systems usually increases thermal and chemical stability, coupled with the lower stability of difluorobenzyl radicals relative to benzyl radicals, OFP derivatives might be predicted to require much higher temperatures to undergo such isomerizations. The inventors were therefore interested to determine whether OFP derivatives would undergo such thermal isomenzations, and if so, what temperatures would be required.

Initially the pseudo ortho dibromo-, pseudo ortho diamino- and dinitro-OFP derivatives were examined, but these compounds proved to be perfectly stable and unchanged when heated neat at 200° C. for 12 hours. After 8 hours at 300° C., the diamino compound had fully decomposed, whilst the dibromo and dinitro compounds showed no isomerization. When the temperature was raised to 350° C. the dinitro compound was extensively charred, but showed traces of isomerization to its pseudo para counterpart, whereas the dibromide was also charred but showed no isomerizations. In contrast, heating the pseudo ortho bis(trifluoroaceamido) AF4 led to no charring, and the sample showed traces of isomerization to its pseudo para isomer.

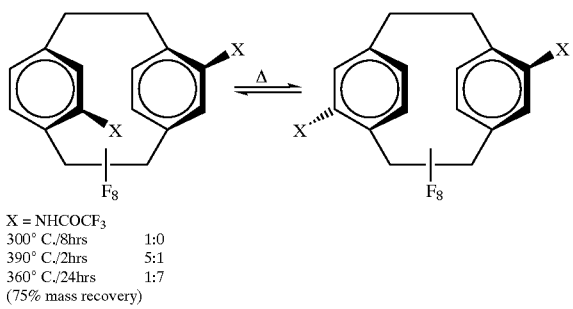

X = NHCOCF₃
300° C./8hrs      1:0
390° C./2hrs      5:1
360° C./24hrs     1:7
(75% mass recovery)

Therefore, the pseudo ortho bis(trifluoroacetamnido)-OFP was heated to 381–390° C. for 2 hours, and was shown by NMR analysis to have converted to a 5:1 ratio of pseudo ortho and pseudo para isomers. Encouraged by this result, this mixture was further heated at 350–360° C. for 24 hrs and the ratio of isomers was found to have changed to 1:7 in favor of the less sterically congested pseudo para isomer. The mass recovery was 75%, with the balance presumably being insoluble polymeric material. Therefore the bridging fluorine atoms in OFP appear to impart 150° C. more kinetic thermal stability to a [2,2] PCP ring system. This not only demonstrates the stabilizing effect of exchanging fluorine for hydrogen, but has serious implications in the use of these fluorinated phanes as chiral ligands, catalysts and auxiliaries, since they display far superior resistance to thermal isomerization than the hydrocarbon analogues, and could therefore be employed at higher temperatures without losing their chirality through thermal racemization.

Characterization

The introduction of a second substituent onto a ring in a [2,2] PCP system can give rise to 7 possible isomers, of which 3 are racemic and 4 are meso (if the two substituents are equivalent). There has been substantial work in this area, and numerous strategies and techniques have evolved that allow unambiguous isomer and structure determination in hydrocarbon [2,2] PCP systems, with $^1$H NMR and mass spectrometry comprising the most powerful tools. Previously the inventors reported that not only were these strategies and techniques equally applicable to the characterization of mono substituted OFP derivatives, but that the OFP derivatives also offered the added bonus of $^{19}$F NMR to distinguish between products. Roche et al., J. ORG. CHEM. (1999) 64, 9137. The inventors have demonstrated that the $^1$H Substituent Chemical Shift (SCS) values previously derived for the amino-OFP system allow accurate prediction of the $^1$H shifts of the three new diamino-OFP products synthesized in accordance with the present invention, and also that the $^{19}$F NMR shifts of the bis(trifluoromethylated) OFP compounds (both hetero- and homo-annular) can also be predicted via the use of the $^{19}$F SCS values derived from monotrifluoromethylated OFP.

Heretobefore, the calculation of $^{19}$F SCS values, and the first demonstration that they may be used to predict the shifts of the bridging fluorines in multiply-substituted OFP derivatives has not been reported.

$^1$H NMR

Due to their symmetric nature, hetero-annularly identically disubstituted [2,2] PCP's display a simple and characteristic $^1$H NMR pattern consisting of one singlet and one AB pattern. All of the disubstituted OFP products described herein also display this feature. The pseudo ortho disubstituted isomer is generally the easiest to recognize since any "gem shift" operates upon the resonance which is a singlet, forcing it downfield, normally clear of the other resonances.

Since it has been demonstrated that amino substituted [2,2] PCP's are the most convenient for NMR investigation, the inventors earlier derived the SCS values for the amino-OFP system (Table 1). Prior work in hydrocarbon [2,2] PCP systems has amply shown that these SCS values are additive, and therefore may be used to calculate proton shifts for multiply substituted systems. The observed 1H shifts can be compared for the three diamino-OFP isomers of the present invention, with those shifts calculated from the SCS values previously dereived (Table 2).

TABLE 1

| Amino OFP SCS values | | | | | | |
|---|---|---|---|---|---|---|
| o | m | p | m' | p' | o' | gem |
| −1.21 | 0.36 | −0.76 | −0.20 | 0.01 | −0.12 | +0.69 |

(Where o = ortho, p = para, m = meta, m' = pseudo meta, p' = pseudo para, o' = pseudo ortho and gem = pseudo geminal).

TABLE 2

| Predicted 'H Chemical Shifts using Amino OFP SCS Values | | | | |
|---|---|---|---|---|
| Compound | Peak Type | SCS Effects | Calculated/ppm | Observed/ppm |
| Pseudo meta | singlet | o + p' | 6.10 | 6.08 |
| DiNH₂ | A | m + gem | 7.63 | 7.57 |
| 3a | B | p + o' | 6.42 | 6.44 |
| Pseudo para | singlet | o + m' | 5.89 | 6.00 |
| diNH₂ | A | m − o' | 6.82 | 6.87 |
| 3b | B | p + gem | 7.23 | 7.04 |
| pseudo ortho | singlet | o + gem | 6.78 | 6.89 |
| diNH₂ | A | m + p' | 6.95 | 7.00 |
| 3c | B | p + m' | 6.34 | 6.36 |

It is clear that there is good agreement between the predicted and observed chemical shifts.

$^{19}$F NMR

Mono-functionalised OFP derivatives exhibit a characteristic four AB pattern in their $^{19}$F NMR spectra, whereas inter-annular identically disubstituted OFP derivatives contain only four different bridging fluorine atoms, which manifest themselves as two A-B patterns. (This is also true for para and ortho oriented intra-annular substituted OFP derivatives). All of the disubstituted OFP derivatives described herein display only two AB patterns in their $^{19}$F NIMR spectra. (Of course, OFP derivatives bearing two different substituents have eight different bridge fluorines that appear as four A-B's, similar to a mono OFP product).

The problem previously described concerning the assignment of fluorine resonances to specific fluorine atoms still exists for the derivatives described here except for the four bis(trifluoromethyl)-OFP derivatives. The "through space" coupling that occurs between a trifluoromethyl ring substituent and the proximate syn bridging fluorines[10] allowed the instant recognition of those bridge fluorines since they appear as quartets. Their partners in the respective A-B patterns could be located by line shape and coupling constant. Thus $F_{1s}/F_{1a}$, $F_{2s}/F_{2a}$ for trifluoromethyl-OFP could be assigned, although the assignment of the remaining 4 fluorines was ambiguous.

Chart 1
Assignment of bridge fluorine resonances in fluoromethyl substituted AF4s 10 and 8a–d

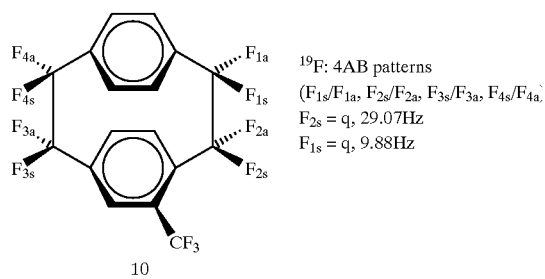

$^{19}$F: 4AB patterns
($F_{1s}/F_{1a}$, $F_{2s}/F_{2a}$, $F_{3s}/F_{3a}$, $F_{4s}/F_{4a}$)
$F_{2s}$ = q, 29.07Hz
$F_{1s}$ = q, 9.88Hz

10

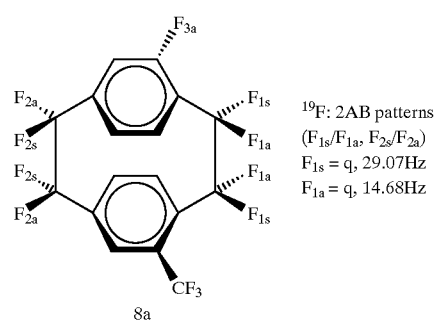

$^{19}$F: 2AB patterns
($F_{1s}/F_{1a}$, $F_{2s}/F_{2a}$)
$F_{1s}$ = q, 29.07Hz
$F_{1a}$ = q, 14.68Hz 8a

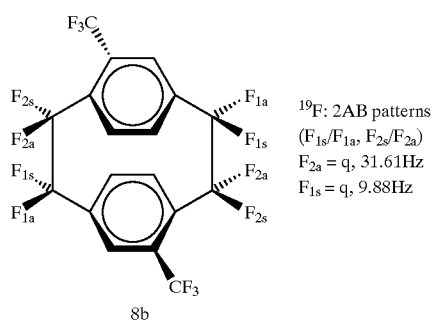

$^{19}$F: 2AB patterns
($F_{1s}/F_{1a}$, $F_{2s}/F_{2a}$)
$F_{2a}$ = q, 31.61Hz
$F_{1s}$ = q, 9.88Hz 8b

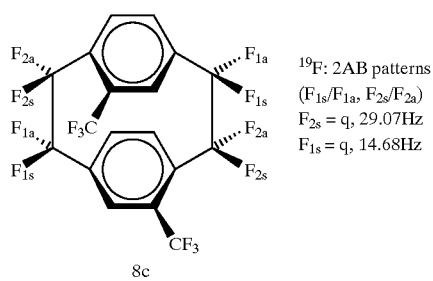

$^{19}$F: 2AB patterns
($F_{1s}/F_{1a}$, $F_{2s}/F_{2a}$)
$F_{2s}$ = q, 29.07Hz
$F_{1s}$ = q, 14.68Hz 8c

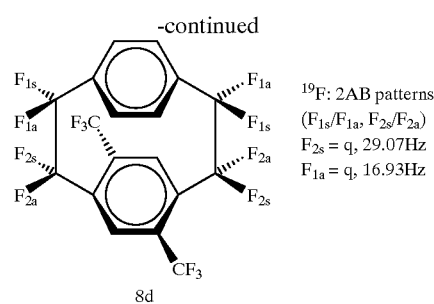

$^{19}$F: 2AB patterns
($F_{1s}/F_{1a}$, $F_{2s}/F_{2a}$)
$F_{2s}$ = q, 29.07Hz
$F_{1a}$ = q, 16.93Hz 8d However, because of symmetry in the bis (trifluoromethyl)-OFP derivatives 8a–d, we can use this coupling interaction to fully assign, for the first time, the bridge fluorine resonances of these systems (and further confirm the accuracy of our isomer assignments). The strategy was to first identify the resonances split in to the large and small quartets, and then find their AB partners. Easiest to identify was the pseudo meta isomer, since this is the only isomer to contain both quartet resonances within the same AB. (This also has the unfortunate consequence that the other two fluorines for this isomer cannot be assigned unambiguously). For the other isomers, the resonances with the larger and smaller quartets were assigned $F_{2s}$ and $F_{1s}$ respectively. Identification of their AB partners via line shape and coupling constant gave $F_{2a}$ and $F_{1a}$. Thus, for the first time, all the fluorine atoms could be assigned to their fluorine resonances.

This presented a situation where there were $^{19}$F chemical shifts and assignments for four disubstituted OFP derivatives, and assignments for half of the shifts for the corresponding monosubstituted derivative. Since it has been demonstrated that $^1$H SCS values are additive for the OFP system, it was projected that the $^{19}$F SCS values should be too, and therefore we should be able to work backwards and assign the remaining four fluorine shifts for the mono derivative. Indeed, one set of assignments for the remaining four fluorines gave much better agreement than the others, as predicted from SCS values taken from the disubstituted systems. These assignments were therefore used in the calculation of the $^{19}$F SCS values for the monotrifluoromethyl OFP system 10.

TABLE 3

$^{19}$F SCS values for 10, in ppm

| $F_{1a}$ | $F_{1s}$ | $F_{2a}$ | $F_{2s}$ | $F_{3a}$ | $F_{3s}$ | $F_{4a}$ | $F_{4s}$ |
|---|---|---|---|---|---|---|---|
| 3.18 | 4.19 | 9.77 | 4.72 | 3.32 | −0.19 | 2.55 | 0.38 |

When these values were used to calculate the shifts for the four bis(trifluoromethyl) derivatives, reasonable agreement was found.

TABLE 4

Calculated $^{19}$F Chemical Shifts for 10, 8a–d.

| Isomer | Assignment | Calculated | Found |
|---|---|---|---|
| Pseudo | $F_{2s}$ | −110.73 | −112.90 |
| Para | $F_{2a}$ | −107.85 | −108.28 |
| 8b | $F_{1s}$ | −110.49 | −111.77 |
|  | $F_{1a}$ | −115.01 | −115.65 |
| Pseudo | $F_{1s}$ | −110.10 | −112.03 |
| Meta | $F^{1a}$ | −104.04 | −105.86 |

TABLE 4-continued

Calculated $^{19}F$ Chemical Shifts for 10, 8a–d.

| Isomer | Assignment | Calculated | Found |
|---|---|---|---|
| 8a | $F_{2s}$ | −115.64 | −118.29 |
|  | $F_{2a}$ | −114.30 | −113.56 |
| pseudo | $F_{2a}$ | −112.90 | −112.23 |
| ortho | $F_{2a}$ | −105.68 | −108.07 |
| 8c | $F_{1s}$ | −114.00 | −114.75 |
|  | $F_{1a}$ | −111.50 | −113.16 |
| para | $F_{2s}$ | −109.96 | −112.85 |
| 8d | $F_{2a}$ | −108.42 | −109.27 |
|  | $F_{1s}$ | −111.26 | −114.83 |
|  | $F_{1a}$ | −114.44 | −113.47 |

Homo-annular Substitution

When a second identical substituent is introduced into the same ring as the first in an OFP, there are only three possible isomeric products, of which two are meso and one is racemic. The three isomers can in principle be differentiated simply by inspection of the format of the $^{19}F$ and $^{1}H$ NMR spectra. The para isomer will result in AB patterns in both the $^{19}F$ and the $^{1}H$ spectra, whereas the ortho isomer will produce $^{19}F$ AB's but singlets in the $^{1}H$ NMR spectrum. The para meta isomer would also produce no AB patterns in the $^{19}F$ spectrum, but would give an AB in the $^{1}H$ spectrum. The only isomer to give rise to AB patterns in both fluorine and proton NMR spectra would be the para isomer. This was observed for dibromo OFP, 5d, and bis(trifluoromethyl) OFP, 8b.

Mass Spectrometry

It has been well documented that mass spectroscopic analysis of [2,2] PCP derivatives provides an excellent method for determination of the number of substituents on each ring. This has also been demonstrated to be the case for mono substituted OFP derivatives, and all the new OFP compounds described herein have mass spectra appropriate to the general rules previously established for both the hydrocarbon and fluorocarbon systems.

This technique provides the simplest way to discriminate between homo- and hetero-annular disubstituted isomers. For example, both the para and pseudo para bis (trifluoromethyl)-OFP'S give the same molecular mass of parent ion of 488. The isomer with a trifluoromethyl group in each ring fragments into two xylylene units of mass 244, whereas the homo-annular isomer fragments into unsubstituted and disubstituted xylylene fragments of mass 176 and 312.

Physical Properties

Reich et al., J. AM. CHEM. SOC. (1969) 91, 3534 derived many correlations between physical properties and relative orientation of disubstituted [2,2] PCP isomers. These general relationships proved equally valid for the OFP systems, and indeed were fundamental to our early characterization work. For example, during column chromatography the disubstituted OFP derivatives always eluted in the same order of pseudo meta/ pseudo para, pseudo ortho, pseudo gem. The pseudo meta and pseudo para isomers could never be separated by column chromatography, although they could be separated on a capillary GC (DB5) column. The pseudo paral pseudo meta isomer mixture could be enriched in one isomer or the other by fractional crystallization or sublimation, with the pseudo para isomer being the least soluble and slowest to sublime. In certain cases, analytical samples of pure pseudo para isomer could be obtained by fractional crystallization. The pseudo para isomer was also the isomer with highest melting point.

Characterization Summary

Both the previously established rules and strategies for characterization of [2,2] PCP and monoOFP derivatives are equally applicable to the identification of disubstituted OFP derivatives, and furthermore allow the discrimination between disubstituted OFP isomers. The use of previously derived $^{1}H$ SCS values allowed the prediction of $^{1}H$ NMR spectra of disubstituted isomers, and also that derived 19F SCS values for trifluoromethyl OFP can be used for the prediction of the $^{19}F$ NMR shifts of the bridge fluorines for bis(trifluoromethylated) OFP isomers. Mass spectroscopy allows the easiest discrimination between homo- and hetero-annular disubstituted isomers.

The following examples are provided for illustrative purposes and are not intended to limit the scope of the claims which follow.

EXAMPLES

Experimental

All NMR spectra were obtained at ambient temperatures in deuterated acetone, and run on a Varian VXR-300 spectrometer with $^{1}H$ at 299.949 MHz with TMS as reference, and at 282.202 MHz for $^{19}F$, using $CFCl_3$ as reference. All reagents, unless otherwise specified, were used as purchased from Aldrich, Milwaukee, Wis. or are Fischer products obtainable from numerous chemical suppliers. Column chromatography was performed using Chromatographic Silica Gel 200–425 mesh as purchased from Fischer. Melting points are uncorrected. Mass spectroscopic analyses were performed on a Finnigan MAT95Q, with an ionizing potential of 70 eV.

Dinitration of OFP

Under a counter current of dry nitrogen, nitronium tetrafluoroborate (22.10 g, 166.17 mmol) was added to octafluoroparacyclophane 1 (10.20 g, 28.98 mmol) dissolved in sulpholane (100 mL), and the reaction was warmed to 80° C. and stirred at this temperature overnight. The reaction mixture was then allowed to cool to room temperature and then added to ice water (400 mL), and the white precipitate was filtered and chromatographed (hexane/ dicholormethane 7/3) to give ($R_f$=0.32) pseudo meta- and pseudo para-dinitro 1,1,2,2,9,9,10,10-octafluoro [2,2] paracyclophanes 2a,b (6.92 g, 54% combined; 1:1 mixture): MS m/z 442 (M$^+$, 6%), 125 (100); Anal. Calcd for $C_{16}H_6F_8N_2O_4$: C, 43.44; H, 1.36; N, 6.33. Found: C, 43.70; H, 1.23; N, 6.21; 2a $^{1}H$ NMR δ 8.009 (s, 1H); 8.009 (m, 1H); 7.783 (d, $^3J$=8.10 Hz, 1H); $^{19}F$ NMR δ −108.806 (d, $^2J$=244.70 Hz, 1F); −111.989 (d, $^2J$=244.70 Hz, 1F); −115.321 (d, $^2J$=239.90 Hz, 1F); −117.317 (d, $^2J$=239.90 Hz, 1F); 2b $^{1}H$ NMR δ 8.009 (s, 1H); 8.009 (m, 1H); 7.783 (d, $^3J$=8.10 Hz, 1H); $^{19}F$ NMR δ −109.829 (d, $^2J$=246.95 Hz, 1F); −113.986 (d, $^2J$=246.95 Hz, 1F); −114.352 (d, $^2J$=237.36 Hz, 1F); −115.028 (d, $^2J$=237.36 Hz, 1F); ($R_f$= 0.20) Pseudo ortho-dinitro-1,1,2,2,9,9,10,10-octafluoro [2,2] paracyclophane 2c (3.46g, 27%): mp 213–215° C. $^{1}H$ NMR δ 8.075 (s, 1H); 7.827 (m, 2H); $^{19}F$ NMR δ −111.023 (d, $^2J$=244.70 Hz, 1F); −112.293 (d, $^2J$=244,70 Hz, 1F); −114.428 (d, $^2J$=242.44 Hz, 1F); −115.582 (d, $^2J$=242.44 Hz, 1F); MS m/z 442 (M$^+$, 10%), 125 (100); Anal. Calcd for $C_{16}H_6F_8N_2O_4$: C, 43.44; H, 1.36; N, 6.33. Found C, 43.70; H, 1.29; N, 6.19. The combined yield of the three dinitro isomers is 81%.

When only 4 equivalents of nitronium tetrafluoroborate was used, the product mixture was subjected to chromatography and shown to contain the mononitrated cyclophane (36%), the pseudo meta- 2a (16%), pseudo para- 2b (16%) and pseudo ortho- 2c (16%) dinitro-1,1,2,2,9,9,10,10-octafluoro [2,2] paracyclophanes.

Pseudo Ortho-diamino-1,1,2,2,9,9,10,10-Octafluoro [2,2] Paracyclophane, 3c

A suspension of pseudo ortho-dinitro-1,1,2,2,9,9,10,10-octafluoro [2,2] paracyclophane 2c (1.30 g, 2.94 mmol) in ethanol/water (1/1 v/v, 50 mL) was stirred for one hour at room temperature. Iron powder (2.00 g, 35.71 mmol) was added, and the reaction mixture was heated to reflux. Concentrated hydrochloric acid (7 mL) was added dropwise to the mixture, and reflux was continued for 4 hours. After this time, the reaction was cooled to room temperature, and was added to ice water (200 mL). The solids thus produced were filtered, and redissolved in chloroform. This chloroform solution was filtered, evaporated and the solid residue was chromatographed (chloroform) to give ($R_f$=0.41) pseudo ortho-diamino-1,1,2,2,9,9,10,10-octafluoro [2,2] paracyclophane 3c (0.91 g, 82%): mp 211° C. (dec.). $^1$H NMR δ 6.999 (d, $^3J$=8.40 Hz, 1H); 6.885 (s, 1H); 6.361 (d, $^3J$=8.40 Hz, 1H); $^{19}$F NMR δ −106.652 (dd, $^2J$=232.56, $^3J$=9.60 Hz, 1F); −114.370 (d, $^2J$=232.56 Hz, 1F); −106.873 (dd, $^2J$=242.44, $^3J$=9.60 Hz, 1F); −111.223 (d, $^2J$=242.44 Hz, 1F); MS m/z 382 (M$^+$, 19%), 191 (100); Anal. Calcd for $C_{16}H_{10}F_8N_2$: C, 50.26; H, 2.62; N, 7.33. Found: C, 50.17; H, 2.41; N, 7.21.

An identical reaction with a 1:1 mixture of pseudo meta- and pseudo para-dinitro-1,1,2,2,9,9,10,10-octafluoro [2,2] paracyclophanes 2a,b gave the corresponding pseudo meta- and pseudo para-diamino-1,1,2,2,9,9,10,10-octafluoro [2,2] paracyclophanes 3a,b in 84% yield. (hexane/chloroform 1/1, $R_f$=0.46): Anal. Calcd for $C_{16}H_{10}F_8N_2$: C, 50.26; H, 2.62; N, 7.33. Found: C, 49.98; H, 2.55; N, 7.07. MS m/z 382 (M$^+$, 21%), 191 (100); 3a, $^1$H NMR δ 7.566 (d, $^3J$=8.40 Hz, 1H); 6.442 (d, $^3J$=8.40 Hz, 1H); 6.084 (s, 1H); $^{19}$F NMR δ 100.315 (m, 2F); −112.440 (d, $^2J$=234.25 Hz, 1F); −116.601 (d, $^2J$=234.25 Hz, 1F); 3b, $^1$H NMR δ 7.038 (d, $^3J$=8.40 Hz, 1H) 6.874 (d, $^3J$ 8.40 Hz, 1H); 6.003 (s, 1H); $^{19}$F NMR δ 103.339 (d, $^2J$=239.33 Hz, 1F); −109.085 (d, $^2J$=239.33 Hz, 1F); −108.562 (d, $^2J$=234.25 Hz, 1F); −109.685 (d, $^2J$=234.25 Hz, 1F).

An ethanol (10 ml) solution containing pseudo ortho dinitro-1,1,2,2,9,9,10,10-octafluoro [2,2] paracyclophane 2c (380 mg, 0.86 mmol), cyclohexene (420 mg, 5.16 mmol) and 10% Pd on carbon (0.2 g) was warmed to reflux, and after 15 minutes of observable reflux, the reaction was evaporated under reduced pressure to a solid residue which was subjected to chromatography (chloroform/hexane 7/3, then chloroform) to give three compounds: ($R_f$=0.46) pseudo ortho nitro-amino-1,1,2,2,9,9,10,10-octafluoro [2,2] paracyclophane 6 (40 mg, 11%): $^1$H NMR δ 8.267 (s, 1H); 7.692 (d, $^3J$=8.40 Hz, 1H); 7.466 (d, $^3J$=8.40 Hz, 1H); 7.107 (d, $^3J$=8.40 Hz, 1H); 6.631 (d, $^3J$=8.40 Hz, 1H); 6.453 (s, 1H); 5.818 (br s 2H, NH$_2$); $^{19}$F NMR δ −105.172 (d, $^2J$=244.70 Hz, 1F); −112.620 (d, $^2J$=244.70 Hz, 1F); −106.128 (d, $^2J$=239.90 Hz, 1F); −110.660 (d, $^2J$=239.90 Hz, 1F); −109.339 (d, $^2J$=244.70 Hz, 1F); −112.615 (d, $^2J$=244.70 Hz, 1F); −111.964 (d, $^2J$=234.82 Hz, 1F); −116.298 (d, $^2J$=234.82 Hz, 1F); MS m/z 412 (M$^+$, 25%), 191 (100). HRMS calcd. for $C_{16}H_8F_8N_2O_2$ 412.0458, found 412.0481. ($R_f$=0.20, chloroform) pseudo ortho diamino-1,1,2,2,9,9,10,10-octafluoro [2,2] paracyclophane 3c (126 mg, 38%), as above. ($R_f$=0.11, chloroform) pseudo ortho hydroxylamino-amino-1,1,2,2,9,9,10,10-octafluoro [2,2] paracyclophane 7 (51 mg, 15%): $^1$H NMR δ 7.609 (s, 1H); 7.118 (d, $^3J$=8.40 Hz, 1H); 6.958 (d, $^3J$=8.40 Hz, 1H); 6.627 (d, $^3J$=8.40 Hz, 1H); 6.373 (d, $^3J$=8.40 Hz, 1H); 6.691 (s, 1H); 8.249 (br s, 1H NH); 7.952 (br s, 1H, OH); 5.337 (br s 2H, NH$_2$); $^{19}$F NMR δ 104.796 (d, 2J=242.16 Hz, 1F); −111.062 (d, $^2J$=242.16 Hz, 1F); −106.012 (d, $^2J$=244.70 Hz, 1F); −111.220 (d, $^2J$=244.70 Hz, 1F); −106.120 (d, $^2J$=235.10 Hz, 1F); −113.514 (d, $^2J$=235.10 Hz, 1F); −106.529 (d, $^2J$=232.28 Hz, 1F); −114.462 (d, $^2J$=232.28 Hz, 1F); MS m/z 398 (M$^+$, 23%), 207 (5), 191 (100); HRMS calcd. for $C_{16}H_{10}F_8ON_2$ 398.0665, found 398.0656.

Typical Diazotization Producedure

A solution of pseudo ortho-diamino-1,1,2,2,9,9,10,10-octafluoro [2,2] paracyclophane 3c (2.00 g, 5.24 mmol) in acetic acid (4 ml) was cooled to 0° C. in an ice/brine bath, ice (1.5 mL) and concentrated 98% sulfuric acid (1.5 mL) were carefully added with stirring, and ensuring the temperature was still below 0° C., sodium nitrite (2.00 g, 28.99 mmol) was added in one batch. The reaction was stirred at this temperature for 2 hours, and then used for the following transformations:

Pseudo Ortho-dibromo-1,1,2,2,9,9,10,10-octafluoro [2,2] Paracyclophane, 5c

An aqueous solution (10 mL) of copper (I) bromide (4.00 g, 27.87 mmol) and 47% hydrobromic acid (10 mL) was warmed to 70° C., and the diazotization solution previously prepared was added in one batch with stirring. The mixture was kept at 70° C. for 1 hour, and then left to cool overnight. The precipitated product was filtered, and chromatographed (hexane/ether 9/1) to give ($R_f$=0.45) pseudo ortho-dibromo-1,1,2,2,9,9,10,10-octafluoro [2,2] paracyclophane 5c (1.60 g, 60%): mp 125–126° C. $^1$H NMR δ 7.845 (s, 1H); 7.520 (d, $^3J$=8.10 Hz, 1H); 7.369 (d, $^3J$=8.10 Hz, 1H); $^{19}$F NMR δ 109.460 (d, 2J=239.90 Hz, 1F); −113.529 (d, $^2J$=239.90 Hz, −110.473 (d, $^2J$=239.90 Hz, 1F); −110.620 (d, $^2J$=239.90 Hz, 1F); MS m/z 510 (M$^+$, 5%), 508 (2), 512 (2), 254 (100), 256 (94); Anal. Calcd for $C_{16}H_6F_8Br_2$: C, 37.65; H; 1.18. Found: C, 37.69; H, 1.15.

An identical reaction with a 1:1 mixture of pseudo meta- and pseudo para-diamino-1,1,2,2,9,9,10,10-octafluoro [2,2] paracyclophanes 3a,b gave the corresponding pseudo meta- and pseudo para-dibromo-1,1,2,2,9,9,10,1 0-octafluoro [2,2] paracyclophanes 5a,b in 65% yield: (hexane/chloroform 9/1, $R_f$=0.62); Anal. Calcd for $C_{16}H_6F_8Br_2$: C, 37.65; H, 1.18. Found: C, 37.44; H, 1.13. MS m/z 510 (M$^+$, 4%), 508 (2), 512 (2), 254 (100), 256 (94). 5a $^1$H NMR δ 7.428 (s, 1H): 7.799 (d, $^3J$=8.10 Hz, 1H); 7.486 (d, $^3J$=8.40 Hz, 1H); $^{19}$F NMR δ 103.640 (d, $^2J$=239.90 Hz, 1F); −113.529 (d, $^2J$=239.90 Hz, 1F); −110.473 (d, $^2J$=239.90 Hz, 1F); −110.620 (d, $^2J$=239.90 Hz, 1F); 5b $^1$H NMR δ 7.165 (s, 1H); 7.895 (d, $^3J$=8.40 Hz, 1H); 7.411 (d, $^3J$=8.40 Hz, 1H); $^{19}$F NMR δ 108.141 (d, $^2J$=239.62 Hz, 1F); −109.137 (d, $^2J$=239.62 Hz, 1F); −110.582 (m, 2F).

Pseudo Ortho-diiodo-1,1,2,2,9,9,10,10-octafluoro [2,2] Paracyclophane, 4c

An aqueous solution (10 mL) of potassium iodide (5.1 g, 30.78 mmol) was warmed to 70° C., and the diazotization solution previously prepared was added in one batch with stirring. The mixture was kept at 70° C. for 1 hour, and then left to cool overnight. The precipitated product was filtered, and chromatographed (hexane/ether 9/1) to give ($R_f$=0.42) pseudo ortho-diiodo-1,1,2,2,9,9,10,10-octafluoro [2,2] paracyclophane 4c (2.47 g, 78%): mp 132–133° C. $^1$H NMR δ 8.157 (s, 1H); 7.457 (d, $^3J$=8.70 Hz, 1H); 7.403 (d, $^3J$=8.70 Hz, 1H); $^{19}$F NMR δ 107.330 (d, $^2J$=237.36 Hz, 1F); −112.570 (d, $^2J$=237.36 Hz, 1F); −109.323 (d, $^2J$=239.90 Hz, 1F); −110.319 (d, $^2J$=239.90 Hz, 1F); MS m/z 604 (M$^+$, 3%), 302 (100). Anal. Calcd for $C_{16}H_6F_8I_2$: C, 31.79; H, 0.99. Found: C, 31.96; H, 0.92.

An identical reaction with a 1:1 mixture of pseudo meta- and pseudo para-diamino-1,1,2,2,9,9,10,10-octafluoro [2,2] paracyclophanes 3a,b gave the corresponding pseudo meta- and pseudo para-diiodo-1,1,2,2,9,9,10,10-octafluoro [2,2] paracyclophanes 4a,b in 78% yield: (hexane/ether 9/1, $R_f$=0.61); Anal. Calcd for $C_{16}H_6F_8I_2$: C, 31.79; H, 0.99. Found: C, 31.86; H, 0.86. MS m/z 604 (M$^+$, 3%), 302 (100). 4a $^1$H NMR δ 7.820 (s, 1H); 7.758 (d,$^3$J=8.10 Hz, 1H); 7.450 (d,$^3$J=8.10 Hz, 1H); $^{19}$F NMR δ 102.046 (d, $^2$J=241.03 Hz, 1F); −105.807 (d, $^2$J=241.03 Hz, 1F); −115.704 (d, $^2$J=239.90 Hz, 1F); −116.452 (d, $^2$J=239.90 Hz, 1F). 4b $^1$H NMR δ 7.573 (s, 1H); 7.994 (d, $^3$J=8.40 Hz, 1H); 7.482 (d, $^3$J=8.40 Hz, 1H); $^{19}$NMR δ 107.109 (d, $^2$J=237.36 Hz, 1F); −109.445 (d, $^2$J=237.36 Hz, 1F); −108.734 (d, $^2$J=237.36 Hz, 1F); −111.322 (d, $^2$J=237.36 Hz, 1F).

Pseudo Ortho-diphenyl-1,1,2,2,9,9,10,10-octafluoro [2,2] Paracyclonhane

Benzene (10 mL) was added to the chilled diazotization solution, and one minute later an aqueous (3 mL) solution of soldium acetate (1.00 g, 12.20 mmol) was added. The bi-phasic mixture was allowed to warm to room temperature overnight with vigorous stirring. Ether was then added, and the bright orange organic phase was separated, dried and evaporated. The crude residue was chromatographed (hexane/dichloromethan 9/1) to give ($R_f$=0.27) 4-phenyl-1,1,2,2,9,9,10,10-octafluoro [2,2] paracyclophane[10] (0.72 g, 32%) and ($R_f$=0.20) pseudo ortho-diphenyl-1,1,2,2,9,9,10,10-octafluoro [2,2] paracyclophane (0.42 g, 16%): $^1$H NMR δ 7.437 (s, 1H); 7.782 (d, $^3$J=8.10 Hz, 1H); 7.641–7.523 (m, 5H); 7.452 (d, $^3$J=8.10 Hz, 1H); $^{19}$F NMR δ 104.750 (d, $^2$J=239.62 Hz, 1F); −113.413 (d, $^2$J=239.62 Hz, 1F); −112.688 (d, $^2$J=244.70 Hz, 1F); −117.061 (d, $^2$J=244.70 Hz, 1F); MS m/z 504 (M$^+$, 8%), 251 (80), 232 (100). HRMS calcd. for $C_{28}H_{16}F_8$ 504.1124, found 504.1157.

Pesudo Ortho-bis(trifluoromethyl)-1,1,2,2,9,9,10,10-octafluoro [2,2] Paracyclophane, 8c A degassed DMF (40 ml) solution containing pseudo ortho-diiodo-1,1,2,2,9,9,10,10-octafluoro [2,2] paracyclophane 4c (3.00 g, 4.97 mmol), methly 2-(fluorosulphonyl)difluoroacetate (9.53 g, 49.67 mmol) and palladium dichloride (40 mg, 0.23 mmol) was warmed to 80° C. under a blanket of nitrogen. Copper (I) bromide (5.33 g, 37.25 mmol) was added in one portion, and the mixture was maintained at that temperature overnight. Then the mixture was cooled to ambient temperature before adding ice water. The mixture was stirred for 30 minutes and then the precipitates were removed by filtration and were subjected to column chromatography (hexane/diethyl ether 9/1) affording ($R_f$=0.3 1) pseudo ortho-iodo-trifluoromethyl-1,1,2,2,9,9,10,10-octafluoro [2,2] paracyclophane 9 (0.27 g 10%): $^1$H NMR δ 7.309 (s, 1H); 6.726 (s, 1H); 6.892 (d, $^3$J=8.40 Hz, 1H); 6.757 (d, $^3$J=8.40 Hz, 1H); 6.705 (d, $^3$J=8.70 Hz, 1H); 6.652 (d, $^3$J=8.70 Hz, 1H); $^{19}$F NMR δ 107.182 (dd, $^2$J=242.16, $^3$J=7.20 Hz, 1F); −112.966 (dq, $^2$J=242.16, $^5$J=29.06 Hz, 1F); −107.635 (dd, $^2$J=239.90, $^3$J=12.10 Hz, 1F); −110.960 (dd, $^2$J=239.90, $^3$J=7.30 Hz, 1F); −108.138 (dd, $^2$J=236.23, $^3$J=12.10 Hz, 1F); −110.315 (dd, $^2$J=236.23, $^3$J=7.30 Hz, 1F); −113.747 (dq, $^2$J=234.82, $^6$J=14.54 Hz, 1F); −114.623(dd, $^2$J=234.82, $^3$J=7.20 Hz, 1F); −59.257 (dd, $^5$J=29.07, $^6$J=14.54 Hz, 3F); MS m/z 546 (M$^+$, 5%), 302 (100), 244 (10). HRMS calcd. for $C_{17}H_6F_{11}I$ 545.9339, found 545.9401; ($R_f$=0.17) Pseudo ortho-bis(trifluoromethyl)-1,1,2,2,9,9,10,10-octafluoro [2,2] paracyclophane 8c (1.65 g, 68%): mp 154–155° C.; $^1$H NMR δ 7.493 (s, 1H); 7.733 (m, 2H); $^{19}$F NMR δ 108.067 (dd, $^2$J=242.16, $^3$J=9.60 Hz, 1F); −112.234 (d,q, $^2$J=242.16, $^5$J=29.07 Hz, 1F); −113.163 (dd, $^2$J=237.36, $^3$J=9.60 Hz, 1F); −114.751 (dq, $^2$J=237.36, $^6$J=14.68 Hz, 1F); −59.160 (dd, $^5$J=29.07, $^6$J=14.68 Hz, 3F); MS m/z 488 (M$^+$,5%), 244 (100); Anal. Calcd for $C_{18}H_6F_{14}$: C, 44.26; H, 1.24. Found: C, 44.24; H, 1.02.

An identical reaction with a 1:1 a mixture of pseudo meta- and pseudo para-diiodo-1,1,2,2,9,9,10,10-octafluoro [2,2] paracyclophanes 4a,b gave the corresponding pseudo meta- and pseudo para-bis(trifluoromethyl)-1,1,2,2,9,9,10,10-octafluoro [2,2] paracyclophanes 8a,b in 80% yield: (hexane/ether 9/1, $R_f$=0.67); Anal. Calcd for $C_{18}H_{16}F_{14}$: C, 44.26; H, 1.24. Found: C, 44.32; H, 1.15. MS m/z 488 (M$^+$, 4%), 244 (100).

There was no evidence of any iodo-trifluoromethyl isomers in this reaction. (It was possible to collect an analytic sample of the more insoluble pseudo para-bis (trifluoromethyl)-1,1,2,2,9,9,10,10-octafluoro [2,2] paracyclophane 8b by fractional crystallization, which had mp 199–200° C.): 8a $^1$H NMR δ 7.824 (s, 1H); 7.710 (d,$^3$J=8.40 Hz, 1H); 7.543 (d,$^3$J=8.40 Hz, 1H); $^{19}$F NMR δ −105.86 (dq, $^2$J=242.16, $^6$J=14.68 Hz, 1F); −112.029 (dq, $^2$J=242.16, $^5$J=29.07 Hz, 1F); −113.562 (d, $^2$J=247.24 Hz, 1F); −118.289 (d, $^2$J=247.24 Hz, 1F); −58.633 (dd, $^5$J=29.07, $^6$J=14.68 Hz, 3F); 8b $^1$H NMR δ 7.850 (s, 1H); 7.693 (d,$^3$J=8.40 Hz, 1H); 7.574 d, $^3$J=8.40 Hz, 1H); $^{19}$F NMR δ 107.280 (dd, $^2$J=242.16, $^3$J=7.06 Hz, 1F); −112.902 (dq, $^2$J=242.16, $^5$J=31.61 Hz, 1F); −111.769 (dq, $^2$J=237.36, $^6$J=9.88 Hz, 1F); −115.648 (dd, $^2$J=237.36, $^3$J=7.06 Hz, 1F); −58.300 (dd, $^5$J=31.61, $^6$J=9.88 Hz, 3F).

4-Trifluoromethyl-1,1,2,2,9,9,10,10-octafluoro [2,2] Paracyclophane, 10

An acetic acid solution (30 mL) containing pseudo ortho-iodo-trifluoromethyl-1,1,2,2,9,9,10,10-octafluoro [2,2] paracyclophane 9 (230 mg, 0.42 mmol) and zinc (110 mg, 1.70 mmol) was refluxed overnight. The mixture was cooled to ambient temperatures and added to ice water (100 mL). The precipitates were collected and subjected to column chromatography (hexane/diethyl ether 8/2) producing ($R_f$=0.56) 4-trifluoromethyl-1,1,2,2,9,9,10,10-octafluoro [2,2] paracyclophane 10 (160 mg, 91%), analytically identical to an authentic sample.[10]

Pseudo Ortho-diacetamido-1,1,2,2,9,9,10,10-octafluoro [2,2] Paracyclophane

A dichloromethane (5 ml) solution of pseudo ortho-diamino-1,1,2,2,9,9,10,10-octafluoro [2,2] paracyclophane 3c (200 mg, 0.52 mmol) was warmed to reflux, and acetyl chloride (2 mL) was added dropwise, and the reaction was refluxed overnight. Rotary evaporation afforded a pale brown residue, which after chromatography (hexane/ether 1/9) gave $R_f$=0.60) pseudo ortho-diacetamido-1,1,2,2,9,9,10,10-octafluoro [2,2] paracyclophane (0.24 g, 97%): mp 199–201° C.; $^1$H NMR δ 7.818 (s, 1H); 7.392 (d, $^3$J=8.10 Hz, 1H); 7.074 (d, $^3$J=8.40 Hz, 1H); 8.854 (br s, 1H, NH); 2.243 (s, 3H, $CH_3$); $^{19}$F NMR δ 107.595 (d, $^2$J=244.70 Hz, 1F); −111.870 (d, $^2$J=244.70 Hz, 1F); −111.439 (d, $^2$J=237.36 Hz, 1F); −114.882 (d, $^2$J=237.36 Hz, 1F); MS m/z 466 (M$^+$, 27%), 446 (40), 233 (12), 191 (100). Anal. Calcd for $C_{20}H_{14}F_8N_2O_2$: C, 51.50; H, 3.00; N, 6.01. Found: C, 51.32; H, 3.05; N, 5.91

An identical reaction with a 1:1 mixture of pseudo meta- and pseudo para-diamino-1,1,2,2,9,9,10,10-octafluoro [2,2] paracyclophanes 3a,b gave the corresponding pseudo meta- and pseudo para-diacetamido-1,1,2,2,9,9,10,10-octafluoro [2,2] paracyclophanes in 84% yield: (hexane/ether 4/6, $R_f$=0.44); Anal. Calcd for $C_{20}H_{14}F_8N_2O_2$: C, 51.50; H, 3.00; N, 6.01. Found: C, 51.38; H, 2.91; N, 5.91. MS m/z 466 (M$^+$, 5%), 446 (42), 233 (22), 191 (100); pseudo meta isomer: $^1$H NMR δ 8.112 (s, 1H); 7.401 (d, $^3$J=8.40 Hz, 1H); 7.013 (d, $^3$J=8.40 Hz, 1H); 8.817 (br s, 1H, NH); 2.251 (s, 3H, $CH_3$); $^{19}$F NMR δ 103.130 (d, $^2$J=247.10 Hz, 1F); −104.959 (d, $^2$J=247.10 Hz, 1F); −115.615 (d, $^2$J=237.36 Hz, 1F); −115.911 (d, $^2$J=237.36 Hz, 1F). pseudo para isomer $^1$H NMR δ 7.808 (s, 1H); 7.401 (d, $^3$J=8.10 Hz, 1H); 7.082 (d, $^3$J=8.10 Hz, 1H); 8.942 (br s, 1H, NH); 2.251 (s, 3H, $CH_3$);

$^{19}$F NMR δ −107.616 (d, $^2$J=244.70 Hz, 1F); −111.836 (d, $^2$J=244.70 Hz, 1F); −113.462 (d, $^2$J=237.36 Hz, 1F); −114.314 (d, $^2$J=237.36 Hz, 1F).

Pseudo Ortho-bis(trifluoroacetamido)-1,1,2,2,9,9,10,10-octafluoro [2,2] Paracyclophane A solution of pseudo ortho-diamino-1,1,2,2,9,9,10,10-octafluoro [2,2] paracyclophane 3c (270 mg, 0.71 mmol) in trifluoroacetic anhydride (4 mL) was refluxed overnight. After this time, rotary evaporation yielded a solid residue that after chromatography (chloroform) afforded ($R_f$=0.64) pseudo ortho-bis(trifluoroacetamido)-1,1,2,2,9,9,10,10-octafluoro [2,2] paracyclophane (0.39 g, 95%): mp 123–124° C.; $^1$H NMR δ 7.550 (s, 1H); 7.470 (d, $^3$J=8.40 Hz, 1H); 7.237 (d, $^3$J=8.40 Hz, 1H); 9.801 (br s 1H, NH); $^{19}$F NMR δ 109.464 (d, $^2$J=247.24, Hz, 1F); −112.265 (d, $^2$J=247.24, Hz, 1F); −113.333 (d, $^2$J=239.90 Hz, 1F); −114.249 (d, $^2$J=239.90, Hz, 1F); −75.832 (s, 3F); MS m/z 574 (M+, 6%), 554 (32), 287 (22), 267(100); Anal. Calcd for $C_{20}H_8F_{14}N_2O_2$: C, 41.81; H, 1.39; N, 4.88. Found: C, 41.64; H, 1.29; N, 4.80.

An identical reaction with a 1:1 mixture of pseudo meta- and pseudo para-diamino-1,1,2,2,9,9,10,10-octafluoro [2,2] paracyclophanes 3a,b gave the corresponding pseudo meta- and pseudo para-bis(trifluoroacetamido)-1,1,2,2,9,9,10,10-octafluoro [2,2] paracyclophanes in 97% yield: (hexane/ether 4/6, $R_f$=0.44); Anal. Calcd for $C_{20}H_8F_{14}N_2O_2$: C, 41.81; H, 1.39; N, 4.88. Found: C, 41.77; H, 1.34; N, 4.81. MS m/z 574 (M$^+$, 3%), 554 (32), 287 (82), 267 (100); pseudo meta isomer: $^1$H NMR δ 7.641 (s, 1H); 7.533 (d, $^3$J=8.40 Hz, 1H); 7.252 (d, $^3$J=8.40 Hz, 1H); 10.117 (brs, 1H, NH); $^{19}$F NMR δ 107.988 (d, $^2$J=247.24 Hz, 1F); −108.255 (d, $^2$=247.24 Hz, 1F); −116.278 (d, $^2$J=239.90 Hz, 1F); −118.013 (d, $^2$J=239.90 Hz, 1F); −75.514 (s, 3F); pseudo para isomer: $^1$H NMR δ 7.765 (s, 1H); 7.406 (d, $^3$J=8.40 Hz, 1H); 7.374 (d, $^3$J=8.40 Hz, 1H); 10.117 (br s, 1H, NH); $^{19}$F NMR δ 111.130 (d, $^2$J=246.95 Hz, 1F); −111.292 (d, $^2$J=246.95 Hz, 1F); −113.375 (d, $^2$J=239.62 Hz, 1F); −115.955 (d, $^2$J=239.62 Hz, 1F); −75.574 (s, 3F).

Pseudo Ortho-diphenyl-1,1,2,2,9,9,10,10-octafluoro [2,2] Paracyclophane

A degassed THF solution (5 mL) containing pseudo ortho-diiodo-1,1,2,2,9,9,10,10-octafluoro [2,2] paracyclophane 4c (300 mg, 0.50 mmol) and palladium dichloride (21 mg, 0.12 mmol) was stirred and brought to reflux under a nitrogen atmosphere. A 1M THF solution of phenyl magnesium bromide (3.0 mL, 3.00 mmol) was added via syringe, and the black solution was refluxed overnight. Evaporation of the solvent was followed by the addition ice water, and the precipitated solids were chromatographed (hexane/dichloromethane 9/1) to give ($R_f$=0.44) 4-phenyl-1,1,2,2,9,9,10,10-octafluoro [2,2] paracyclophane[10] (43 mg, 20%), and $R_f$=0.37) pseudo ortho-diphenyl-1,1,2,2,9,9,10,10-octafluoro [2,2] paracyclophane (53 mg, 21%): $^1$H NMR δ 7.437 (s, 1H); 7.782 (d, $^3$J=8.10 Hz, 1H); 7.641–7.523 (m, 5H); 7.452 (d, $^3$J=8.10 Hz, 1H); $^{19}$F NMR δ −104.750 (d, $^2$J=239.62 Hz, 1F); −113.413 (d, $^2$J=239.62 Hz, 1F); −112.688 (d, $^2$J=244.70 Hz, 1F); −117.061 (d, $^2$J=244.70 Hz, 1F); MS m/z 504 (M$^+$, 8%), 251 (80), 232 (100). HRMS calcd. for $C_{28}H_{16}F_8$ 504.1124, found 504.1157.

Para Dibromi-1,1,2,2,9,9,10,10-octafluoro [2,2] Paracyclophane, 5d

A trifluoroacetic acid solution (3 ml) containing 1,1,2,2,9,9,10,10-octafluoro [2,2] paracyclophane 1(1.00 g, 2.84 mmol) and N-bromo-succinamide (2.02 g, 11.35 mmol) was stirred magnetically in a flask protected by a silica drying tube. After 5 minutes, 98% sulfuric acid (1 mL) was added, and left to stir for 16 hrs. After this time analysis by $^{19}$F NMR and TLC showed the presence of starting material, mono-bromo OFP and several dibromide isomers, one of which seemed predominant. The reaction was warmed to 80° C. and left another 12 hrs. The mixture was cooled to ambient temperatures, and added to 100 mL of ice water. The pale yellow precipitate was subjected to column chromatography (hexane/chloroform 50/1), and gave ($R_f$=0.36) para dibromo-1,1,2,2,9,9,10,10-octafluoro [2,2] paracyclophane 5d (0.65 g, 55%): mp 159–161° C.; $^1$H NMR δ 7.416 (s, 1H); 7.970 (d, $^3$J=8.40 Hz, 1H); 7.481 (d, $^3$J=8.40 Hz, 1H); $^{19}$F NMR δ 110.194 (d, $^2$J=237.36 Hz, 1F); −112.642 (d, $^2$J=237.36 Hz, 1F); −111.499 (m, 2F); MS m/z 508 (M$^+$, 6%), 510 (13), 512 (6), 334 (5), 254 (53), 256 (49), 176 (100); Anal. Calcd for $C_{16}H_6F_8Br_2$: C, 37.65; H, 1.18. Found: C, 37.81; H, 1.19; ($R_f$=0.20) A mixture of monobromo-, dibromi-(2 isomers) and tribromo-(3 isomers)-1,1,2,2,9,9,10,10-octafluoro [2,2] paracyclophanes (0.172 g). GLCMS indicted that the dibromo isomers in the second fraction showed one isomer each of hetero- and homo-annular disbtribution, whilst the tribromides all contained 2 bromines on one ring and 1 in the other. This second fraction was not further analyzed.

Para Bis(trifluoromethyl)-1,1,2,2,9,9,10,10-octafluoro [2,2] Paracyclophane, 8d

A degassed DMF (20 mL) solution containing para-dibromo-1,1,2,2,9,9,10,10-octafluoro [2,2] paracyclophane 5d (0.53 g, 1.04 mmol) and methyl 2-(fluorosulphonyl) difluoroacetate (0.80 g, 4.16 mmol) was warmed to 100° C. under a blanket of nitrogen. Copper (I) bromide (0.59 g, 4.16 mmol) was added in one portion, and the mixture was maintained at that temperature overnight. Then the mixture was cooled to ambient temperature before adding ice water. The mixture was stirred for 30 minutes and then the precipitates were removed by filtration and were subjected to column chromatography (hexane/diethyl ether 9/1) affording ($R_f$=0.72) para-bis(trifluoromethyl)-1,1,2,2,9,9,10,10-octafluoro [2,2] paracyclophane 8d (66 mg, 13%): mp 125–126° C.; $^1$H NMR δ 7.810 (s, 1H); 7.427 (m, 2H); $^{19}$F NMR δ 109.271 (dd, $^2$J=244.67, $^3$J=9.88 Hz, 1F); −112.848 (dq, $^2$J=244.67, $^5$J=29.07 Hz, 1F); −113.468 (dd, $^2$J=232.54, $^3$J=9.88 Hz, 1F); −114.830 (dq, $^2$J=232.54, $^6$J=16.93 Hz, 1F); −59.187 (dd, $^5$J=29.07, $^6$J=16.93 Hz, 3F); MS m/z 488 (M$^+$, 3%), 312 (3), 176 (100); Anal. Calcd for $C_{18}H_6F_{14}$: C, 44.26; H, 1.23. Found: C, 44.47; H, 1.19; ($R_f$=0.40) 4-Trifluoromethyl-1,1,2,2,9,9,10,10-octafluoro [2,2] paracyclophane 10 (74 mg, 17%), whose characterization was identical to an authentic sample.[10]

Thermal Isomerization

A tube containing pseudo ortho-bis(trifluoroacetamido)-1,1,2,2,9,9,10,10-octafluoro [2,2] paracyclophane (90 mg, mmol) was evacuated, sealed immersed in a Woods metal heating bath at 381–390° C. for 2 hours. After this time, the tube was cooled, opened and shown by $^{19}$F NMR to contain both pseudo ortho- and pseudo para-bis(trifluoroacetamido)-1,1,2,2,9,9,10,10-octafluoro [2,2] paracyclophanes in a 5:1 ratio. This material was placed into another identical tube, and again evacuated, sealed and immersed into the Woods metal heating bath and heated at 350–363° C. for 24 hours. The resulting product mixture was shown by $^{19}$F NMR to now contain a 1:7 ratio of pseudo ortho- and pseudo para-bis(trifluoroacetamido)-1,1,2,2,9,9,10,10-octafluoro [2,2] paracyclophanes. Integration versus an internal standard of trifluorotoluene showed the mass balance of the two isomers was 75%.

What is claimed is:

1. A process for the preparation of derivatives of octafluoro-[2,2]paracyclophane, which comprises the steps of:

reacting octafluoro-[2,2]paracyclophane with a nitronium reagent to provide dinitro octafluoro-[2,2]paracylophane isomers;

reducing said dinitro octafluoro-[2,2]paracylophane isomers by reacting the dinitro octafluoro-[2,2]paracylophane isomers with iron powder in concentrated hydrochloric acid to provide pseudo-meta, pseudo-para and pseudo ortho isomers of diamino octafluoro-[2,2]paracylophane in good yield; and reacting said diamino octafluoro-[2,2]paracylophane isomers with an aqueous halogen solution to provide pseudo-meta, pseudo-para and pseudo ortho isomers of hetero-annular dihalo-octafluoro- [2,2]paracylophane in good yield.

2. The process as recited in claim 1, wherein the step of reacting said dinitro octafluoro-[2,2]paracylophane isomers exist as pseudo-meta, pseudo-para and pseudo-ortho isomers.

3. The process as recited in claim 2, wherein said dinitro octafluoro-[2,2]paracylophane isomers are formed in a 1:1:1 ratio.

4. The process of claim 1, wherein the dihalo-octafluoro-[2,2]paracylophane isomers formed in the second reacting step comprise dibromo-octafluoro-[2,2]paracylophane and diiodo-octafluoro-[2,2]paracylophane isomers.

5. The process of claim 1, wherein diamino octafluoro-[2,2]paracylophane isomers were prepared in isolated yields of from 82–84%.

6. The process of claim 4, wherein the dibromo-octafluoro [2,2]paracylophane and diiodo-octafluoro-[2,2]paracylophane isomers were prepared in isolated yields of from 60–78%.

7. The process of claim 1, wherein said nitration agent consists of 5 equivalents of $NO_2PF_4$ in sulpholane at 80° C.

8. Isomeric derivatives of octafluoro-[2,2]paracyclophane, having the structures:

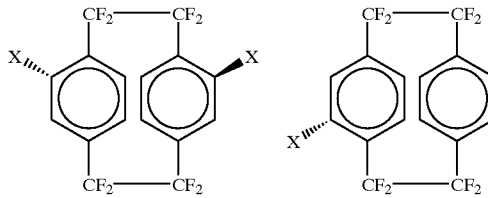

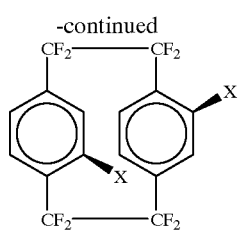

-continued wherein X=$NH_2$, Br, or I.

9. The isomeric derivatives according to claim 8, wherein X is $NH_2$.

10. The isomeric derivatives according to claim 8, wherein X is Br.

11. The isomeric derivatives according to claim 8, wherein X is I.

12. The isomeric derivatives according to claim 9, wherein said isomeric derivatives are formed by reacting octafluoro-[2,2]paracyclophane with a nitronium reagent to provide dinitro octafluoro-[2,2]paracyclophane isomers; reducing said mononitro octafluoro-[2,2]paracyclophane by reacting the dinitro octafluoro-[2,2]paracyclophane with iron powder in concentrated hydrochloric acid to provide hetero-annular isomeric diamino octafluoro-[2,2] paracyclophane products.

13. The isomeric derivatives according to claim 12, wherein said diamino octafluoro-[2,2]paracyclophane products are formed in a 1:1:1 ratio.

14. The isomeric derivatives according to claim 13, wherein said diamino octafluoro-[2,2]paracyclophane products are reacted with an aqueous halogen solution to provide homo-annular dihalo-octafluoro-[2,2]paracyclophane isomers in high yields.

15. The isomeric derivatives according to claim 8, wherein said derivatives exist as pseudo-meta, pseudo-para and pseudo-ortho isomers.

16. The isomeric derivatives according to claim 8, for use as versatile precursors for the production of novel homo- and hetero-annular disubstituted octafluoro-[2,2]paracylcophane derivatives.

* * * * *